(12) United States Patent
Parce et al.

(10) Patent No.: US 6,379,974 B1
(45) Date of Patent: Apr. 30, 2002

(54) MICROFLUIDIC SYSTEMS

(75) Inventors: John Wallace Parce, Palo Alto; Anne R. Kopf-Sill, Portola Valley; Luc J. Bousse, Menlo Park, all of CA (US)

(73) Assignee: Caliper Technologies Corp., Mountain View, CA (US)

(*) Notice: Subject to any disclaimer, the term of this patent is extended or adjusted under 35 U.S.C. 154(b) by 0 days.

(21) Appl. No.: 09/377,682

(22) Filed: Aug. 19, 1999

Related U.S. Application Data

(62) Division of application No. 08/971,854, filed on Nov. 17, 1997.
(60) Provisional application No. 60/031,406, filed on Nov. 19, 1996.

(51) Int. Cl.[7] .................................................. G01N 1/18
(52) U.S. Cl. ........................ 436/180; 204/600; 204/601; 204/643; 422/100; 422/101; 422/102
(58) Field of Search ........................ 422/68.1, 99, 100, 422/101, 102; 436/180; 204/600, 601, 643

(56) References Cited

U.S. PATENT DOCUMENTS

| | | |
|---|---|---|
| 4,390,403 A | 6/1983 | Batchelder |
| 4,908,112 A | 3/1990 | Pace |
| 5,126,022 A | 6/1992 | Soane et al. |
| 5,250,263 A | 10/1993 | Manz |
| 5,296,114 A | 3/1994 | Manz |
| 5,480,614 A | 1/1996 | Kamahori |
| 5,498,392 A | 3/1996 | Wilding et al. |
| 5,571,410 A | 11/1996 | Swedberg et al. |
| 5,585,069 A | 12/1996 | Zanzucchi et al. |
| 5,593,838 A | 1/1997 | Zanzucchi et al. |
| 5,599,432 A | 2/1997 | Manz et al. |
| 5,603,351 A | 2/1997 | Cherukuri et al. |
| 5,632,876 A | 5/1997 | Zanzucchi et al. |
| 5,635,358 A | 6/1997 | Wilding et al. |
| 5,637,469 A | 6/1997 | Wilding et al. |
| 5,755,942 A | 5/1998 | Zanzucchi et al. |
| 5,770,029 A | * 6/1998 | Nelson et al. |
| 5,779,868 A | 7/1998 | Parce et al. |
| 5,800,690 A | 9/1998 | Chow et al. |
| 5,824,204 A | 10/1998 | Jerman |
| 6,001,229 A | * 12/1999 | Ramsey |
| 6,074,827 A | * 6/2000 | Nelson et al. |

FOREIGN PATENT DOCUMENTS

| | | |
|---|---|---|
| WO | WO9604547 | 2/1996 |
| WO | WO9702357 | 1/1997 |

OTHER PUBLICATIONS

Dasgupta, P.K. et al., "Electroosmosis: A Reliable Fluid Propulsion System for Flow Injection Analysis," *Anal. Chem.* 66:1792–1798 (1994).

Jacobson, S.C. et al., "Fused Quartz Substrates for Microchip Electrophoresis," *Anal. Chem.* 67:2059–2063 (1995).

Manz, A. et al., "Electroosmotic pumping and electrophoretic separations for miniaturized chemical analysis systems," *J. Micromech. Microeng.* 4:257–265 (1994).

Manz, A. et al., "parallel Capillaries for High Throughput in Electrophoretic and Electroosmotic Drug Discovery Systems," *Transducers 97*, Chicago, IL Jun. 16–19, 1997 2:915–918 (1997).

(List continued on next page.)

*Primary Examiner*—Jan Ludlow
(74) *Attorney, Agent, or Firm*—Matthew B. Murphy

(57) ABSTRACT

The present invention generally provides microfluidic devices and systems that utilize electrokinetic material transport systems to selectively control and direct the transport of materials through and among complex arrangements of integrated, interconnected microscale channels disposed within integrated body structures. Channels are sized and positioned to provide equal resistance in different paths.

7 Claims, 15 Drawing Sheets

OTHER PUBLICATIONS

Mccormick, R.M. et al., "Microchannel electrophoretic separations of DNA in Injection–molded plastic substrates," *Anal. Chem.* 69:2626–2630 (1997).

Ramsey, J.M. et al., "Microfabricated chemical measurement systems," *Nature Med.* 1:1093–1096 (1995).

Seiler, K. et al., "Planar Glass Chips for Capillary Electrophoresis: Repetitive Sample Injection, Quantitation, and Separation Efficiency," *Anal. Chem.* 65:1481–1488 (1993).

Seiler, K. et al., "Electroosmotic Pumping and Valveless Control of Fluid Flow Within a Manifold of Capillaries on a Glass Chip," *Anal. Chem.* 66:3485–3491 (1994).

Slater, G.W. et al., "Electrophoretic resolution versus fluctuations of the lateral dimensions of a capillary," *Electrophoresis* 16:771–779 (1995).

Woolley, A.T. et al., "High–Speed DNA Genotyping Using Microfabricated Capillary Array Electrophoresis Chips," *Anal. Chem.* 69:2181–2186 (1997).

* cited by examiner

SERIAL

PARALLEL

SERIAL

CONVERTER

MULTIPLE SERIAL

MICROFLUIDIC SYSTEMS

CROSS-REFERENCE TO RELATED APPLICATIONS

This application is a divisional of U.S. Pat. application No. 08/971,854, filed Nov. 17, 1997, which claimed priority to Provisional Application No. 60/031,406, filed Nov. 19, 1996, each of which is hereby incorporated herein by reference in their entirety for all purposes.

BACKGROUND OF THE INVENTION

In the electronics industry, manufacturers and developers have sought to increase product performance, speed and capacity, as well as the profits derived therefrom, through miniaturization. Likewise, the pharmaceutical, biotechnology and related industries have sought similar benefits through miniaturization and automation of operations and processes performed in those industries. Performance of more and more operations in less and less space has thus become of primary interest in these industries. Space, therefore, while perhaps not the final frontier, remains an area that invites substantial exploitation.

To achieve this miniaturization the biotechnology and pharmaceutical industries have recently applied some of the same technologies which proved effective in the electronics industry, such as photolithography, wet chemical etching, laser ablation, etc., to the microfabrication of fluidic devices for use in chemical and biological applications. For example, as early as 1979, researchers reported the fabrication of a miniature gas chromatograph on a silicon wafer (discussed in Manz et al., Adv. in Chromatog. (1993) 33:1–66, citing Terry et al., IEEE Trans. Electron. Devices (1979) ED-26: 1880). These fabrication technologies have since been applied to the production of more complex devices for a wider variety of applications.

There have been additional reports of microfabrication of fluidic devices in these solid substrates for a variety of uses. The most prominent of uses for this technology has been in the area of microcapillary electrophoresis. Microcapillary electrophoresis typically involves the introduction of a macromolecule containing sample, e.g., nucleic acids or proteins, into one end of a capillary tube that also contains a separation medium such as agarose, polyacrylamide or the like. A potential is applied across the capillary to draw the sample through the channel, separating the macromolecules in the sample based upon their relative motility in the separation medium, which can vary by the size or charge on the macromolecules. While these methods typically employed fused silica capillaries for the performance of electrophoretic methods, in more recent efforts, the fused silica capillary has been replaced by an etched channel in a solid planar substrate. A covering substrate provides the last wall of the capillary. Early discussions of the use of planar chip technology for fabrication of microfluidic devices are provided in Manz et al., Trends in Anal. Chem. (1990) 10(5): 144–149 and Manz et al., Adv. in Chromatog. (1993) 33:1–66, which describe the fabrication of fluidic devices and particularly microcapillary devices, in silicon and glass substrates.

The transport and direction of materials, e.g., fluids, samples, analytes, buffers and reagents, within microfabricated devices has generally been carried out by: (1) the incorporation of mechanical micropumps and valves within the device (see, Published U.K. Patent Application No. 2 248 891, Published European Patent Application No. 568 902, U.S. Pat. Nos. 5,271,724, 5,277,556 and 5,171,132); (2) the use of electric fields to move a fluid containing charged elements through the device (see, e.g., Published European Patent Application No. 376 611, Harrison et al., Anal. Chem. (1992) 64:1926–1932, Manz et al. J. Chromatog. (1992) 593:253–258, U.S. Pat. No. 5,126,022 to Soane); (3) the use of acoustic energy to move fluid samples within devices by the effects of acoustic means (see, Published PCT Application No. 94/05414 to Northrup and White); or (4) the application of external pressure to move fluids within the device (see, e.g., U.S. Pat. No. 5,304,487 to Wilding et al.).

As microfluidic systems become more complex, the ability to accurately control and direct the fluid flow within these systems becomes more and more difficult. It would therefore be desirable to provide improved microfluidic devices or systems that take into account the problems associated with these complex microfluidic systems. The present invention meets these and a variety of other needs.

SUMMARY OF THE INVENTION

The present invention is generally directed to microfluidic systems and methods for use in performing a plurality of parallel operations within a single microfluidic system. Such parallel analyses may be performed on a single sample material, or upon multiple sample materials.

In one aspect, the present invention provides a microfluidic device, that comprises a body structure, which includes a plurality of integrated microscale channels disposed therein. The plurality of integrated microscale channels include at least a first transverse channel, and at least first and second side channels disposed on a first side of the transverse channel. Each of the first and second side channels have first and second ends, where the first ends intersect the transverse channel, and the second ends are in electrical communication with at least a first electrode. Also included are at least third and fourth side channels disposed on a second side of the transverse channel. Each of the third and fourth side channels similarly have first and second ends, where the first ends intersect the transverse channel, and the second ends are in electrical communication with at least a second electrode. The side channels are provided whereby the electrical current path between the first electrode and the transverse channel through the first side channel provides substantially equal resistance to a resistance between the first electrode and the transverse channel through the second side channel.

The microfluidic devices described herein are generally useful for providing for controlled material transport within a large number of integrated channels, with a minimum of control nodes. For example, in a related aspect, the present invention provides a microfluidic device for controllably transporting material among a plurality of intersecting microscale channels. The device comprises a body structure having a channel network disposed therein. The channel network comprises a plurality of intersecting microscale channels, which include n channel intersections, and x unintersected channel termini, wherein n is greater than or equal to x, provided that x is at least 2 and n is at least 3. An electrical power supply is also included to supply a separate electrical potential to each of the unintersected termini, or electrical control nodes, of the plurality of microscale channels, whereby the electrical potential supplied at each of the x unintersected channel termini controls material transport at the n intersections. In preferred aspects, the power supply utilizes a controlled current at multiple electrodes to affect material transport. Examples of such power supplies are described in detail in U.S. Pat. No. 5,800,690, and PCT Publication WO 98/00707, published Jan. 8, 1998, incorporated herein by reference.

In an additional related aspect, the present invention provides a microfluidic system, which includes a microfluidic device as described above. In particular, the system includes a microfluidic device that comprises a body structure having a plurality of integrated channels disposed in the body structure, the plurality of integrated channels. The integrated channels include at least a first transverse channel, and at least first and second side channels disposed on a first side of the transverse channel. Each of the first and second side channels have first and second ends, where the first ends intersect the transverse channel, and the second ends are in fluid communication with at least a first source of first material. Also included in the integrated channels are at least third and fourth side channels disposed on a second side of the transverse channel. Each of the third and fourth channels have first and second ends, where the first ends are in fluid communication with the transverse channel, and the second ends are in fluid communication with a waste reservoir. The system also includes a material transport system for transporting a second material into the transverse channel, and for transporting portions of the second material into the third and fourth channels. The transport is affected by directing a flow of first material from the first source, through the first and second channels into the transverse channel.

The present invention also provides methods of transporting materials in a serial to parallel material transport operation. In particular, the present invention provides a method of directing one or more materials serially introduced into a microscale channel, into a plurality of parallel channels fluidly connected to the microscale channel. The method comprises providing a microfluidic device having at least a first microscale transverse channel, at least first and second microscale side channels intersecting a first side of the transverse channel, at least third and fourth microscale side channels intersecting a second side of the transverse channel. One or more materials are serially introduced into the first transverse channel. At least a portion of the one or more materials are then directed into the at least third and fourth channels by directing material into the transverse channel from the first and second channels.

In a further aspect, the present invention provides a method of controllably transporting a material among a plurality of interconnected microscale channels. The method comprises providing a microfluidic device having a body structure that includes a channel network disposed therein. The channel network includes a plurality of intersecting microscale channels, which comprise n channels and x unintersected channel termini, wherein x is less than or equal to n, and provided that x is at least 2 and n is at least 3. A separate selected electrical potential is applied to each of the x reservoirs, whereupon material is controllably moved at and through the n intersections.

BRIEF DESCRIPTION OF THE FIGURES

FIG. 2 schematically illustrates conversion of materials in a serial orientation in a single microscale channel into a parallel orientation in a number of microscale channels.

DETAILED DESCRIPTION OF THE INVENTION

The present invention generally provides microfluidic devices and systems that utilize electrokinetic material transport systems to selectively control and direct the transport of materials through and among complex arrangements of integrated, interconnected microscale channels disposed within integrated body structures.

As used herein, the term "microscale" or "microfabricated" generally refers to structural elements or features of a device which have at least one fabricated dimension in the range of from about 0.1 $\mu$m to about 500 $\mu$m. Thus, a device referred to as being microfabricated or microscale will include at least one structural element or feature having such a dimension. When used to describe a fluidic element, such as a passage, chamber or conduit, the terms "microscale," "microfabricated" or "microfluidic" generally refer to one or more fluid passages, chambers or conduits which have at least one internal cross-sectional dimension, e.g., depth, width, length, diameter, etc., that is less than 500 $\mu$m, and typically between about 0.1 $\mu$m and about 500 $\mu$m. In the devices of the present invention, the microscale channels or chambers preferably have at least one cross-sectional dimension between about 0.1 $\mu$m and 200 $\mu$m, more preferably between about 0.1 $\mu$m and 100 $\mu$m, and often between about 0.1 $\mu$m and 20 $\mu$m. Accordingly, the microfluidic devices or systems prepared in accordance with the present invention typically include at least one microscale channel, usually at least two intersecting microscale channels, and often, three or more intersecting channels disposed within a single body structure. Channel intersections may exist in a number of formats, including cross intersections, "T" intersections, or any number of other structures whereby two channels are in fluid communication.

The body structure of the microfluidic devices described herein typically comprises an aggregation of two or more separate layers which when appropriately mated or joined together, form the microfluidic device of the invention, e.g., containing the channels and/or chambers described herein. Typically, the microfluidic devices described herein will comprise a top portion, a bottom portion, and an interior portion, wherein the interior portion substantially defines the channels and chambers of the device.

Figure 1:
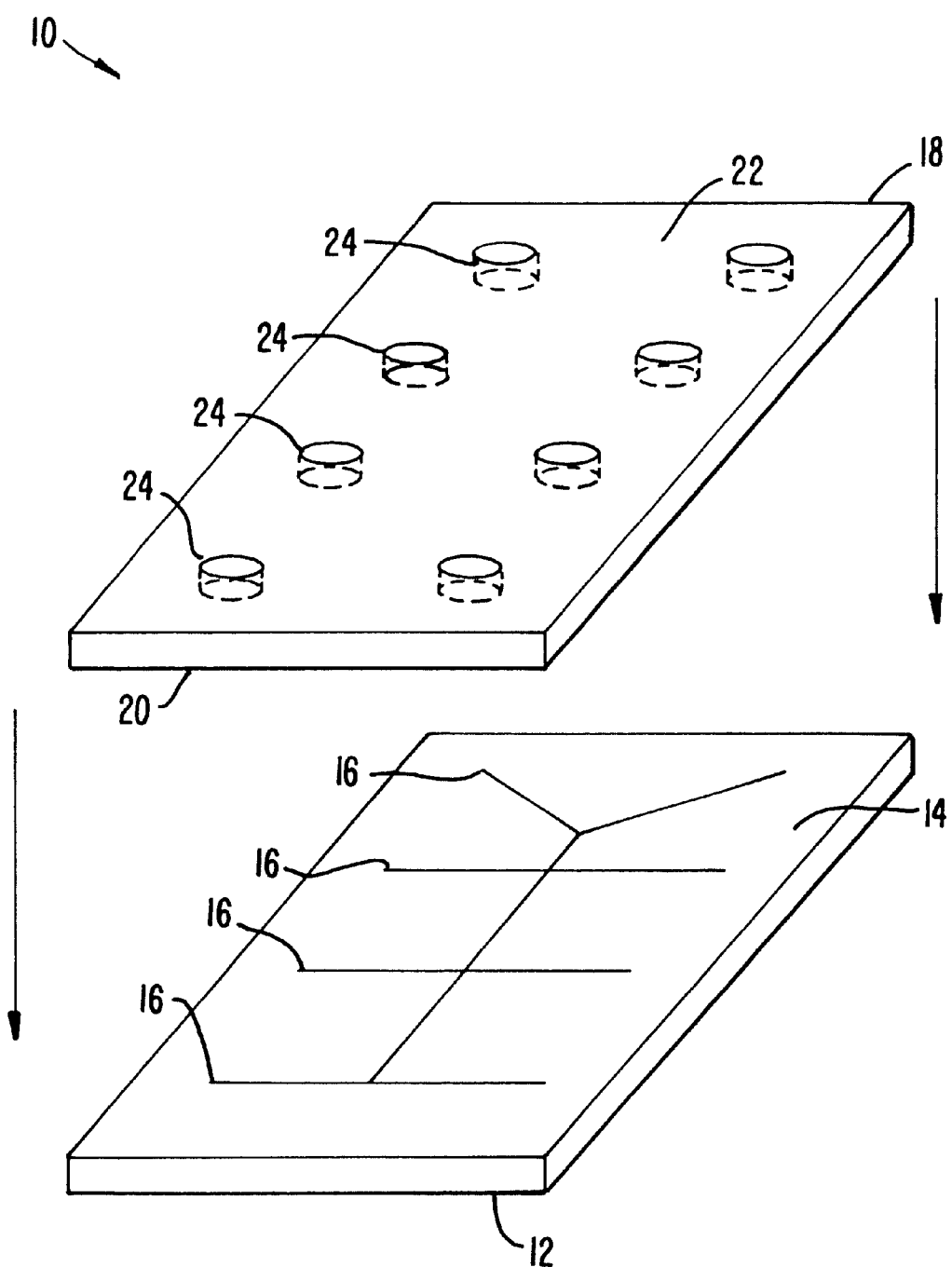
FIG. 1 schematically illustrates an example of multi-layer construction of a typical microfluidic device.

In preferred aspects, the microfluidic devices include multi-layer body structures in which the microscale channels are disposed, one example of which is illustrated in FIG. 1. The bottom portion of the device 12 comprises a solid substrate that is substantially planar in structure, and which has at least one substantially flat upper surface 14. A variety of substrate materials may be employed as the bottom portion. Typically, because the devices are microfabricated, substrate materials will be selected based upon their compatibility with known microfabrication techniques, e.g., photolithography, wet chemical etching, laser ablation, air abrasion techniques, LIGA methods, injection molding, embossing, and other techniques. The substrate materials are also generally selected for their compatibility with the full range of conditions to which the microfluidic devices may be exposed, including extremes of pH, temperature, salt concentration, and application of electric fields. Accordingly, in some preferred aspects, the substrate material may include materials normally associated with the semiconductor industry in which such microfabrication techniques are regularly employed, including, e.g., silica based substrates, such as glass, quartz, silicon or polysilicon, as well as other substrate materials, such as gallium arsenide and the like. In the case of semiconductive materials, it will often be desirable to provide an insulating coating or layer, e.g., silicon oxide, over the substrate material, and particularly in those applications where electric fields are to be applied to the device or its contents. The production of microfluidic devices according to the present invention, uses for such devices, methods of operating such devices, and peripheral devices for use with such microfluidic devices, are generally described in U.S. Pat. application Ser. Nos. 08/691,632, filed Aug. 2, 1996, 08/671,987, filed Jun. 28, 1996, now U.S. Pat. No. 5,942,443, U.S. Pat. Nos. 5,699,157 and 5,800,690 and provisional U.S. patent application Ser. No. 60/015,498, filed Apr. 16, 1996, each of which is hereby incorporated herein by reference in its entirety for all purposes.

In additional preferred aspects, the substrate materials comprise polymeric materials, e.g., plastics, such as polymethylmethacrylate (PMMA), polycarbonate, polytetrafluoroethylene (TEFLON™), polyvinylchloride (PVC), polydimethylsiloxane (PDMS), polysulfone, and the like. Such polymeric substrates are readily manufactured using available microfabrication techniques, as described above, or from microfabricated masters, using well known molding techniques, such as injection molding, embossing or stamping, or by polymerizing the polymeric precursor material within the mold (See U.S. Pat. No. 5,512,131). Such polymeric substrate materials are preferred for their ease of manufacture, low cost and disposability, as well as their general inertness to most extreme reaction conditions. Again, these polymeric materials often include treated surfaces, e.g., derivatized or coated surfaces, to enhance their utility in the microfluidic system, or may be selected so as to provide an appropriate surface charge, e.g., provide enhanced fluid direction, e.g., as described in U.S. Pat. No. 5,885,470, and which is incorporated herein by reference in its entirety for all purposes.

The channels and/or chambers of the microfluidic devices are typically fabricated into the upper surface of the bottom substrate or portion 12, as microscale grooves or indentations 16, using the above described microfabrication techniques. The top portion or substrate 18 also comprises a first planar surface 20, and a second surface 22 opposite the first planar surface 20. In the microfluidic devices prepared in accordance with the methods described herein, the top portion also includes a plurality of apertures, holes or ports 24 disposed therethrough, e.g., from the first planar surface 20 to the second surface 22 opposite the first planar surface.

The first planar surface 20 of the top substrate 18 is then mated, e.g., placed into contact with, and bonded to the planar surface 14 of the bottom substrate 12, covering and sealing the grooves and/or indentations 16 in the surface of the bottom substrate, to form the channels and/or chambers (i.e., the interior portion) of the device at the interface of these two components. The holes 24 in the top portion of the device are oriented such that they are in communication with at least one of the channels and/or chambers formed in the interior portion of the device from the grooves or indentations in the bottom substrate. In the completed device, these holes function as reservoirs for facilitating fluid or material introduction into the channels or chambers of the interior portion of the device, as well as providing ports at which electrodes may be placed into contact with fluids within the device, allowing application of electric fields along the channels of the device to control and direct fluid transport within the device.

In many embodiments, the microfluidic devices will include an optical detection window disposed across one or more channels and/or chambers of the device. Optical detection windows are typically transparent such that they are capable of transmitting an optical signal from the channel/chamber over which they are disposed. Optical detection windows may merely be a region of a transparent cover layer, e.g., where the cover layer is glass or quartz, or a transparent polymer material, e.g., PMMA, polycarbonate, etc. Alternatively, where opaque substrates are used in manufacturing the devices, transparent detection windows fabricated from the above materials may be separately manufactured into the device.

These devices may be used in a variety of applications, including, e.g., the performance of high throughput screening assays in drug discovery, immunoassays, diagnostics, genetic analysis, and the like. As such, the devices described herein, will often include multiple sample introduction ports or reservoirs, for the parallel or serial introduction and analysis of multiple samples. Alternatively, these devices may be coupled to a sample introduction port, e.g., a pipettor, which serially introduces multiple samples into the device for analysis. Examples of such sample introduction systems are described in e.g., U.S. patent application Ser. No. 08/761,575, filed Dec. 6, 1996 and U.S. Pat. 5,880,071, each of which was filed on Dec. 6, 1996, and is hereby incorporated by reference in its entirety for all purposes.

As noted previously, the devices, methods and systems described herein, employ electrokinetic material transport systems, and preferably, controlled electrokinetic material transport systems to controllably direct materials among the various channels contained within the device. As used herein, "electrokinetic material transport systems" include systems which transport and direct materials within an interconnected channel and/or chamber containing structure, through the application of electrical fields to the materials, thereby causing material movement through and among the channel and/or chambers.

Such electrokinetic material transport and direction systems include those systems that rely upon the electrophoretic mobility of charged species within the electric field applied to the structure. Such systems are more particularly referred to as electrophoretic material transport systems. Other electrokinetic material direction and transport systems rely upon the electroosmotic flow of fluid and material within a channel or chamber structure, which results from the application of an electric field across such structures. In brief, when a fluid is placed into a channel which has a surface bearing charged functional groups, e.g., hydroxyl groups in etched glass channels or glass microcapillaries, those groups can ionize. In the case of hydroxyl functional groups, this ionization, e.g., at neutral pH, results in the release of protons from the surface and into the fluid, creating a concentration of protons at near the fluid/surface interface, or a positively charged sheath surrounding the bulk fluid in the channel. Application of a voltage gradient across the length of the channel, will cause the proton sheath to move in the direction of the voltage drop, i.e., toward the negative electrode.

"Controlled electrokinetic material transport and direction," as used herein, refers to electrokinetic systems as described above, which employ active control of the voltages applied at multiple, i.e., more than two, electrodes. Rephrased, such controlled electrokinetic systems concomitantly regulate voltage gradients applied across at least two intersecting channels. Controlled electrokinetic material transport is described in Published PCT Application No. WO 96/04547, published Feb. 15, 1996, to Ramsey, which is incorporated herein by reference in its entirety for all purposes. In particular, the preferred microfluidic devices and systems described herein, include a body structure which includes at least two intersecting channels or fluid conduits, e.g., interconnected, enclosed chambers, which channels include at least three unintersected termini. The intersection of two channels refers to a point at which two or more channels are in fluid communication with each other, and encompasses "T" intersections, cross intersections, "wagon wheel" intersections of multiple channels, or any other channel geometry where two or more channels are in such fluid communication. An unintersected terminus of a channel is a point at which a channel terminates not as a result of that channel's intersection with another channel, e.g., a "T" intersection. In preferred aspects, the devices will include at least three intersecting channels having at least four unintersected termini. In a basic cross channel structure, where a single horizontal channel is intersected and crossed by a single vertical channel, controlled electrokinetic material transport operates to controllably direct material flow through the intersection, by providing constraining flows from the other channels at the intersection. For example, assuming one was desirous of transporting a first material through the horizontal channel, e.g., from left to right, across the intersection with the vertical channel. Simple electrokinetic material flow of this material across the intersection could be accomplished by applying a voltage gradient across the length of the horizontal channel, i.e., applying a first voltage to the left terminus of this channel, and a second, lower voltage to the right terminus of this channel, or by grounding the right terminus. However, this type of material flow through the intersection would result in a substantial amount of diffusion at the intersection, resulting from both the natural diffusive properties of the material being transported in the medium used, as well as convective effects at the intersection.

In controlled electrokinetic material transport, the material being transported across the intersection is constrained by low level flow from the side channels, e.g., the top and bottom channels. This controlled material transport at the intersections is accomplished by applying a slight voltage gradient along the path of material flow, e.g., from the top and bottom termini of the vertical channel, toward the right terminus. The result is a "pinching" of the material flow at the intersection, which prevents the diffusion of the material into the vertical channel. The pinched volume of material at the intersection may then be injected into the vertical channel by applying a voltage gradient across the length of the vertical channel, i.e., from the top terminus to the bottom terminus. In order to avoid any bleeding over of material from the horizontal channel during this injection, a low level of flow is directed back into the side channels, resulting in a "pull back" of the material from the intersection.

In addition to pinched injection schemes, controlled electrokinetic material transport is readily utilized to create virtual valves, which include no mechanical or moving parts. Specifically, with reference to the cross intersection described above, flow of material from one channel segment to another, e.g., the left arm to the right arm of the horizontal channel, can be efficiently regulated, stopped and reinitiated, by a controlled flow from the vertical channel, e.g., from the bottom arm to the top arm of the vertical channel. Specifically, in the 'off' mode, the material is transported from the left arm, through the intersection and into the top arm by applying a voltage gradient across the left and top termini. A constraining flow is directed from the bottom arm to the top arm by applying a similar voltage gradient along this path (from the bottom terminus to the top terminus). Metered amounts of material are then dispensed from the left arm into the right arm of the horizontal channel by switching the applied voltage gradient from left to top, to left to right. The amount of time and the voltage gradient applied dictates the amount of material that will be dispensed in this manner. Each of the above material flow profiles, e.g., pinched, gated or pull-back, are examples of controlled material transport at intersections.

Controlled electrokinetic material transport at intersections also permits/encompasses relatively precise mixing of materials from two channels that meet at a common intersection using electrokinetic material transport systems. Specifically, by applying appropriate electrokinetic forces to each channel, e.g., at a desired ratio, one can dictate relatively precisely, the ratio of materials being mixed from each of the channels.

Although described for the purposes of illustration with respect to a single four-way, cross intersection, in accordance with the present invention, such systems are readily adapted for more complex channel geometries. For example, as set forth in U.S. patent application Ser. Nos. 08/671,987 and 08/671,986, now U.S. Pat. No. 5,779,868 both filed Jun. 28, 1996 and incorporated herein by reference, microfluidic devices are often utilized to perform a large number of parallel operations on a sample or a number of samples, i.e., to screen biological samples, to screen test compounds for drug discovery, and the like. To carry out these operations, a substrate will typically employ an array of parallel channels interconnected by one or more common channels. Fluids required for the subject reaction, e.g., samples or reagents, are directed along one or more of the common channels, and are delivered to each of the parallel channels. The materials must then be converted from the serial orientation in the common channel, into a parallel orientation in the various parallel channels. The present invention provides devices, systems and methods for accomplishing this conversion.

In one aspect, the present invention generally provides novel substrate channel layouts that ensure controlled material transport in interconnected parallel channels, i.e., connected to a common transverse channel, and thereby facilitates the direction of fluids or samples serially introduced into a microfluidic device, into a number of separate parallel channels. The direction of materials from a serial orientation in one channel, to a parallel orientation in a plurality of channels within these microfluidic devices is generally referred to herein as "serial to parallel conversion."

Serial to parallel conversion of materials within a microfluidic device is important for a number of reasons. For example, where one is performing a number of separate analyses on a single sample, serial to parallel conversion can be used to aliquot the single sample among a number of separate channels in a microfluidic device, wherein a different analysis or assay is performed in each different channel. Alternatively, a number of physically discrete and different samples, e.g., drug candidates, diagnostic samples, or the like, may be serially introduced into a single device and allocated among a number of different parallel channels subjecting the samples to the same basic analysis.

Figure 2A:
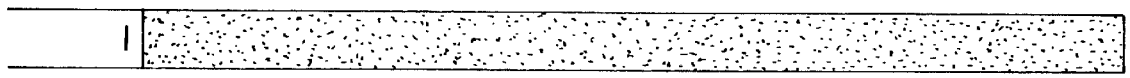
FIGS. 2A–2D illustrate alternate applications of serial to parallel conversion of sample fluids using the microfluidic devices employing the chip layouts or designs of the present invention.
Figure 2A:
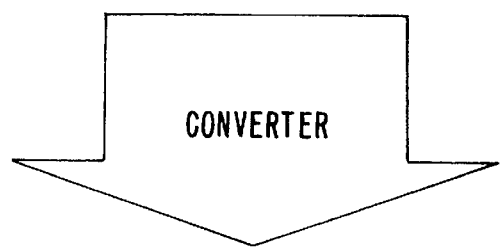
Figure 2A:
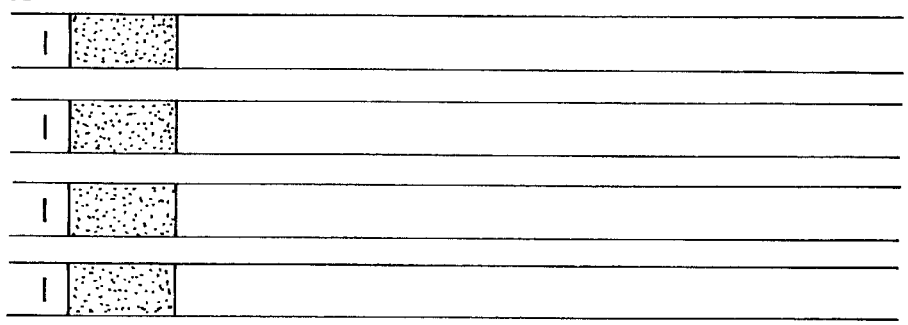
Figure 2B:
Figure 2B:
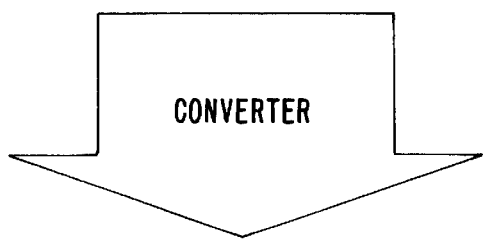
Figure 2B:
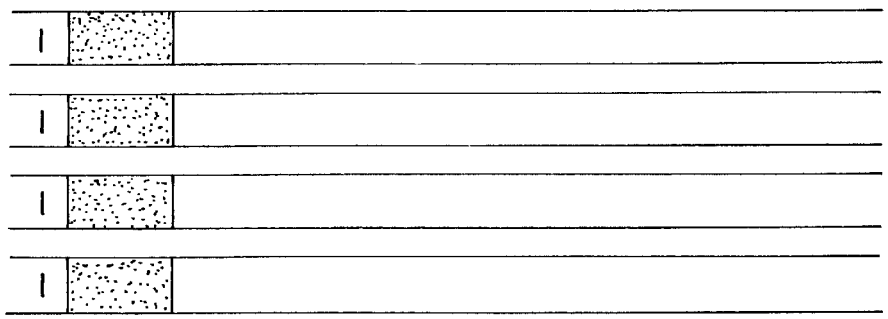
Figure 2C:
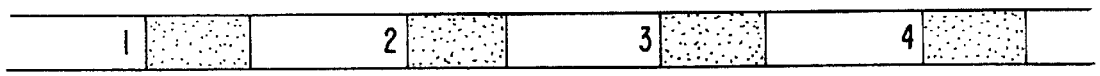
Figure 2C:
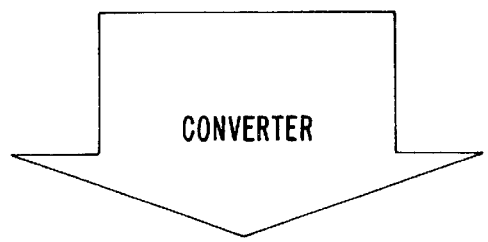
Figure 2C:
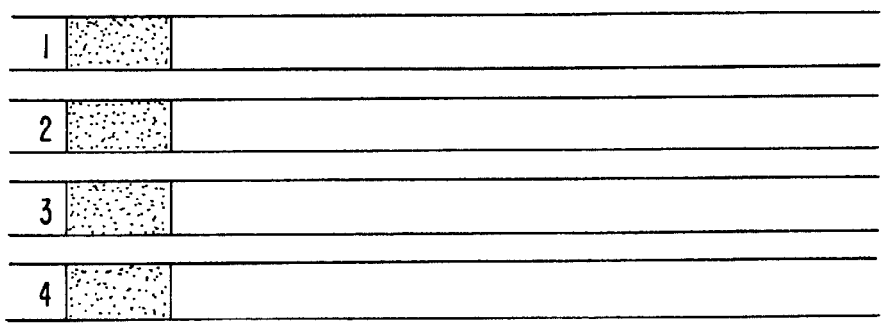
Figure 2D:
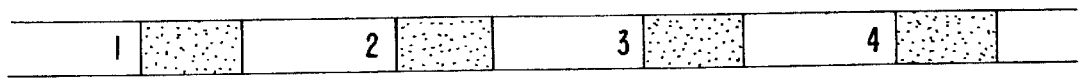
Figure 2D:
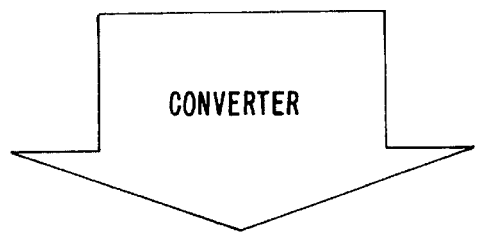
Figure 2D:
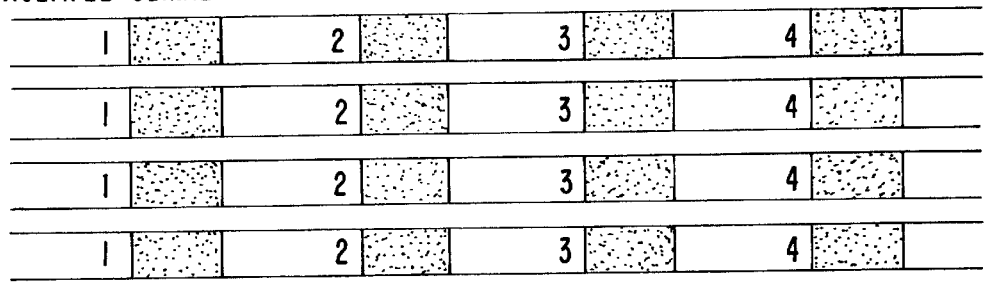

Schematic illustrations of serial to parallel conversions are shown in FIGS. 2A–2D. For example, in FIG. 2A, a single plug of sample material (1) is shown being converted to a plurality of separate aliquots of the sample material, in a series of parallel channels. Alternatively, as shown in FIG. 2B, separate aliquots of the same sample material, provided in a serial orientation in a single channel are allocated to each of several separate parallel channels. In a particularly useful aspect, as shown in FIG. 2C, a plurality of different compounds (1, 2, 3 and 4) are serially introduced into a microscale channel (top) and then are each redirected to a separate parallel channel for separate analysis. FIG. 2D also illustrates a particularly useful application of serial to parallel conversion where a plurality of different samples (1, 2, 3 and 4) are serially introduced into a microfluidic channel, and are allocated and redirected among a number of parallel channels, wherein each parallel channel receives a portion of each of the samples and reflects the serial orientation originally presented (bottom). This is a particularly useful application in the ultra high throughput analysis of large numbers of sample materials, e.g., where a plurality of different samples (e.g., 1, 2, 3 and 4) may be subjected to a plurality of different analyses (e.g., in each separate parallel channel).

While serial to parallel conversion is an important aspect of fluid control in microfluidic systems, it is not without its problems. For example, as noted above, material transport in electrokinetic systems is driven by current flow between electrodes disposed at different points in the system. Furthermore, resistance in the fluid channels, which is inversely related to current flow, changes as a function of path length and width, and thus, different length channels will have different resistances. In systems having multiple parallel current paths, e.g., channels, interconnected to a common channel, material transport along each of the parallel channels is most easily controlled by providing electrode pairs at the termini of each of the parallel channels. These pairs of electrodes are then used to provide matching currents in each of the parallel channels. Specifically, use of common electrodes for all of the parallel channels, without more, can result in the formation of transverse electric fields among the various parallel channels. These transverse electrical fields can destroy the ability of the devices to direct fluid flow within these devices. Specifically, the current, and thus the fluid flow, will follow the path of least resistance, e.g., the shortest path, between electrodes. By presenting matching currents in these parallel channels, one avoids the formation of these transverse electrical fields from one parallel channel to the next. While the use of separate pairs of electrodes for each channel will obviate the problem of transverse electrical fields, production of devices incorporating this many electrodes, and control systems for controlling the electrical potential applied at each of these electrodes would prove prohibitively complex. This is particularly true where one is dealing with tens, hundreds or even thousands of parallel channels in a single small-scale device, e.g., 1–10 cm$^2$. Accordingly, the present invention provides microfluidic devices for affecting serial to parallel conversion, by ensuring that current flow through each of a plurality of parallel channels is either equal, or is at some preselected level, without requiring separate electrodes for each separate parallel channel.

Generally, the devices and systems of the present invention accomplish this controlled electrokinetic transport in interconnected parallel channel structures by ensuring that the current flow through each of the parallel channels is substantially equal. Maintaining substantially equal current flow is generally accomplished by controlling the amount of resistance along any given current path. This, in turn, may be accomplished by controlling the path length or width, or a combination of the two, at least over a portion of the current path.

In addition to permitting control of materials in interconnected parallel channel networks without the formation of transverse electric fields, as noted above, the present invention also provides the advantage of permitting control of material transport in a large number of interconnected channels, and at a plurality of channel intersections, with a minimum number of electrical control nodes in the fluidic system (e.g., electrodes).

By "control of material transport" at an intersection is meant the precise control of material direction and flow rates from the channel segments into the intersection with which these segments are in fluid communication. Typically, such controlled material transport utilizes the controlled input of current into the intersection from the various channel segments that communicate with that intersection. Such precise control is used to precisely control the flow of material into the intersection from each of the channel segments, or alternatively, to prevent material from flowing into the intersection from one or more channel segments, through the control of current at the unintersected channel termini in the overall channel network. In the first illustrated example, controlled material transport at an intersection involves the simultaneous application of current flow from at least two channel segments into a particular intersection. Thus, in this respect, controlled material transport at an intersection involves more than unidirectional flow of material through an intersection, e.g., from one channel segment into the intersection and out through another channel segment. Instead, material is transported into the intersection through at least two channel segments, and out through a third. Examples of this type of controlled transport at an intersection include, e.g., mixing flow, pinched flow, gated flow and/or 'pull-back' flow of material.

Figure 9A:
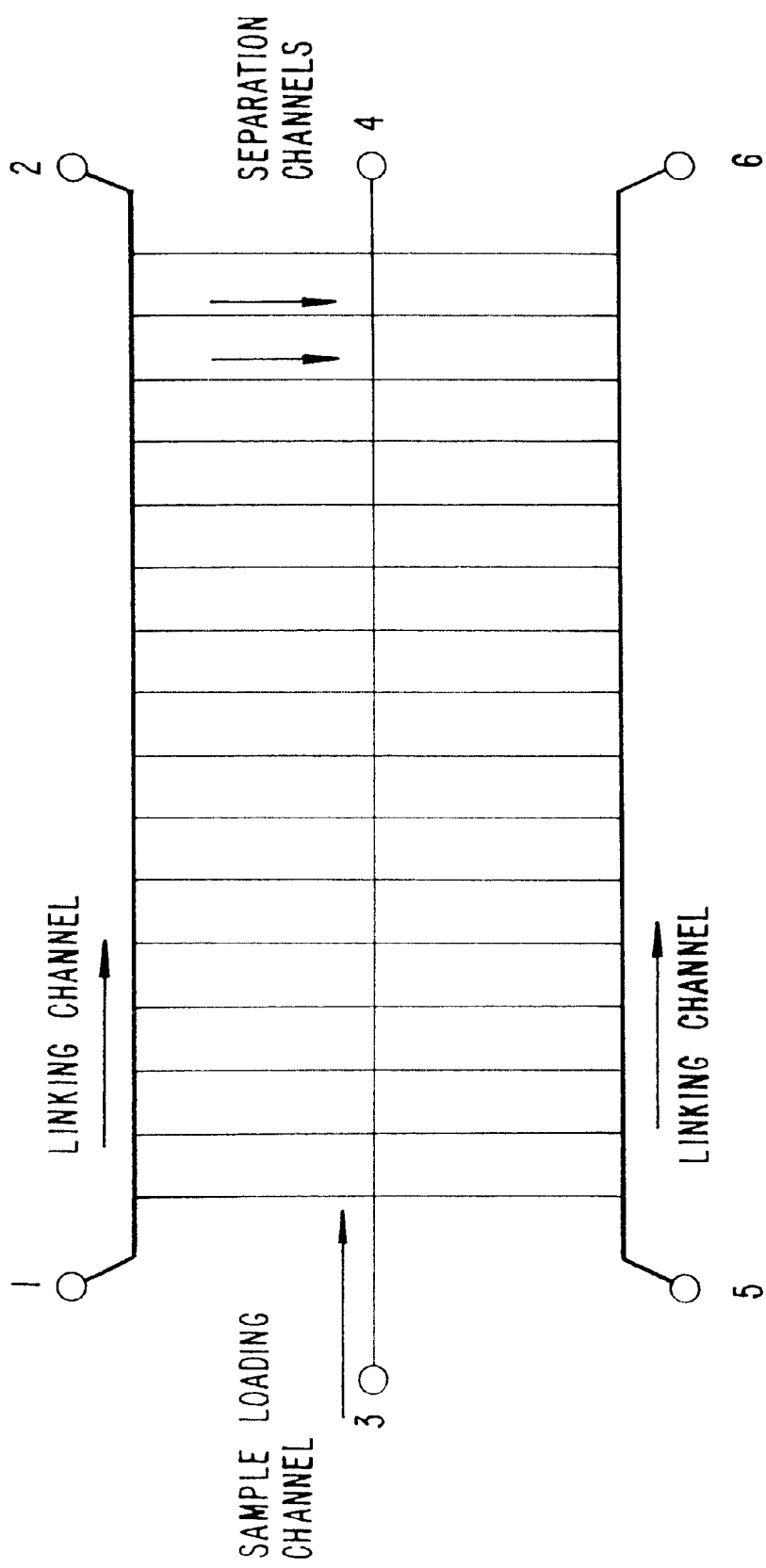
FIGS. 9A–C schematically illustrates a process and device structure for converting a sample serially introduced into a channel, into a plurality of parallel channels intersecting the first channel.
Figure 9B:
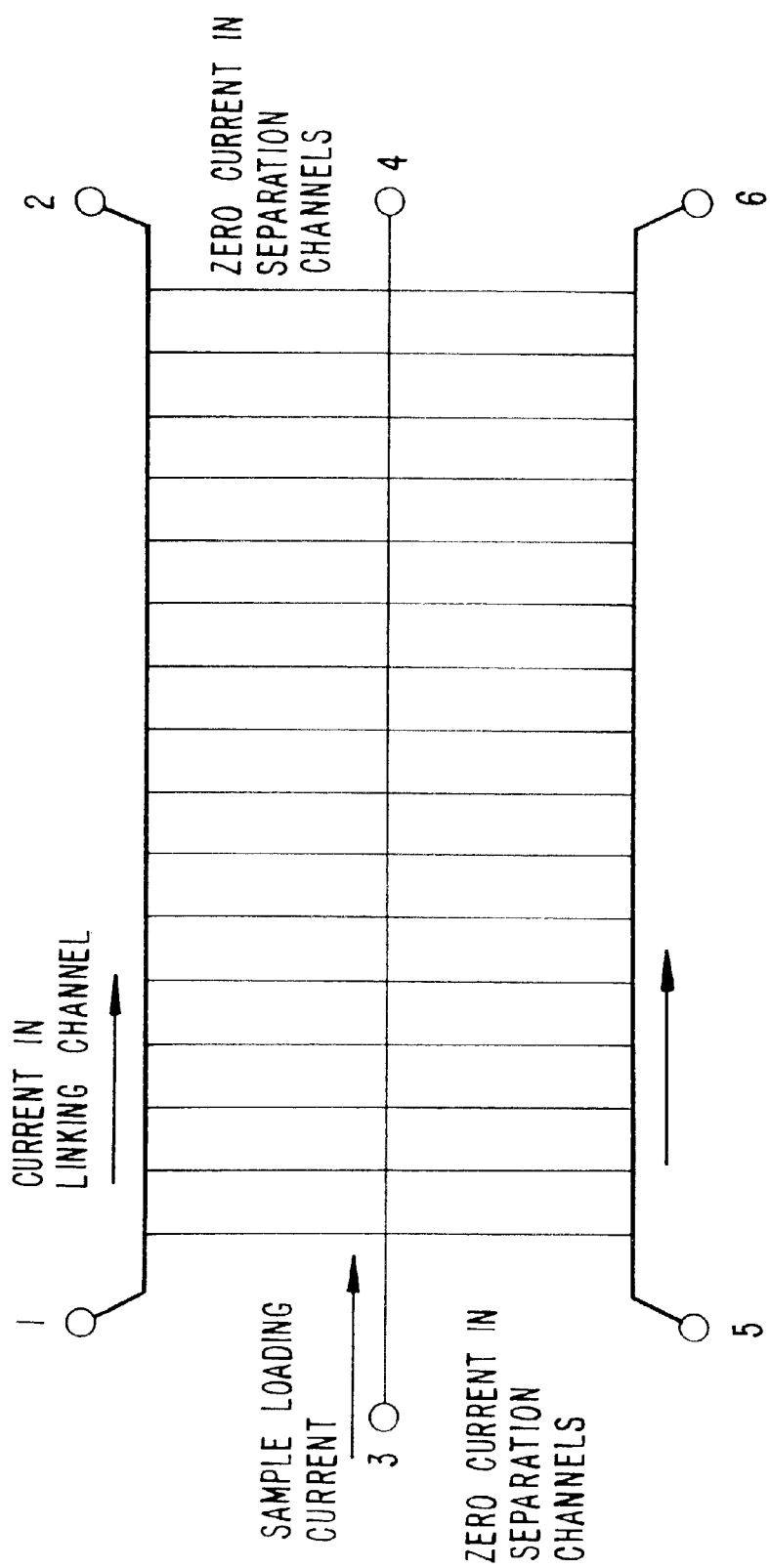
Figure 9C:
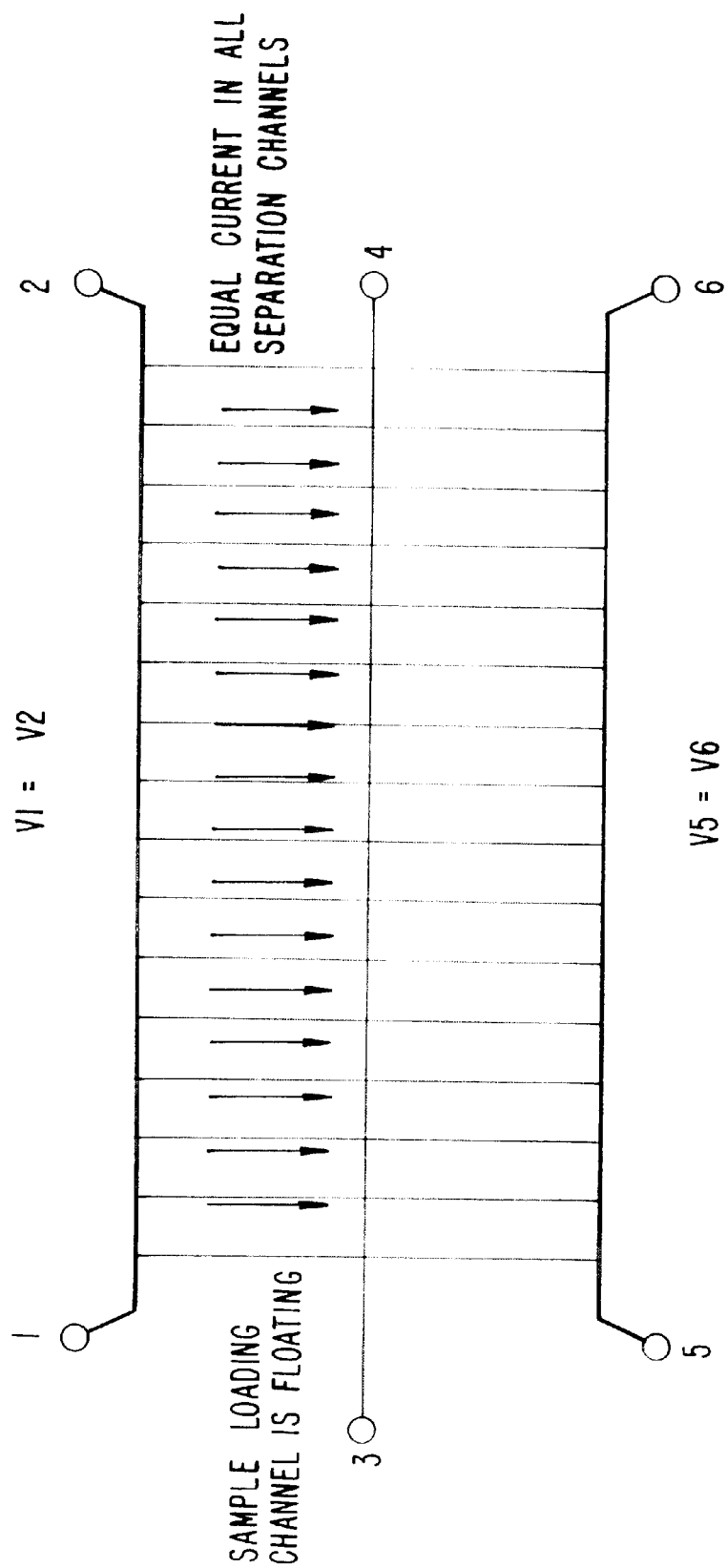

Control of material transport at an intersection also utilizes precise current control to prevent materials from being flowed into a given intersection. This type of control is schematically illustrated in a parallel channel structure, e.g., as shown in FIGS. 9A–9C. As shown in FIG. 9A, the device is schematically illustrated having a central sample loading channel (connecting reservoirs 3 and 4), and two linking channels (connecting reservoirs 1 and 2, and 5 and 6, respectively) also termed transverse channels. Connecting each of the linking channels and intersecting the sample loading channel in the process are a number of separation channels. As described in substantially greater detail, herein, the separation channels, typically in combination with the linking channels are designed to provide equivalent electrical resistance between electrodes, regardless of the parallel channel used.

In operation, sample(s) are loaded through the sample loading channel by applying a current through the sample loading channel. In order to prevent current looping through the separation channels and linking channels, equivalent currents are applied through the linking channels, such that the net current through the separation channels is zero (FIG. 9B). Relative applied voltages are indicated for each of the reservoir/electrodes, e.g., V1, V2, etc. Pinched flow in the sample loading channel can also be provided by applying a slightly smaller voltage gradient across the linking channels, causing a very slight level of current flow through the separation channels from the linking channels into the sample loading channel. For example, a 10 mA current can be applied to reservoir 3. A pinching flow is applied by applying 10 mA at reservoirs 1 and 5 and only taking out 9.9 mA at reservoirs 2 and 6. The remaining 0.1 mA forces flow toward the sample loading channels by taking off 10.2 mA at reservoir 4.

Sample(s) disposed across the intersection of the sample loading channel and the separation channels is/are then injected into each of the separation channels and separated by applying the current from reservoirs 1 and 2 to reservoirs 5 and 6 (FIG. 9C).

This same operation is illustrated with respect to the device shown in FIG. 3, as follows. In brief, a material is transported through channel 202 across that channel's intersections with channels 208–244, by applying a current through that channel, e.g., a voltage gradient between reservoirs 204 and 206. Material transport at these intersections is controlled by applying a matching current through channels 224 and 246, thereby preventing current flow through any of the side channels 208–244. This is described in greater detail, below.

Thus, control of material transport at an intersection is characterized by the ability to control the level of current flow into an intersection from each of the channel segments that communicate with that intersection, including preventing current flow from or into some of those channel segments.

As used herein, the term "material" generally refers to molecular species that are typically fluid borne. For example, in systems utilizing electroosmotic material transport, the material of interest typically includes the bulk fluid and all of its constituent elements that are being transported. In electrophoretic material transport systems, however, the material that is being transported includes charged molecular species, including the material of interest, e.g., sample components, as well as ionic species that are moving under such electrophoretic control, e.g., buffer salts, ions and the like.

Typically, control of material transport at a particular intersection by electrokinetic means, requires a separate electrode at the unintersected terminus of each channel that communicates at the intersection. Thus, where a microfluidic system has a single intersection made up of four intersecting channels (a typical four-way or crossing intersection), four electrodes, typically disposed at the unintersected termini of the four channels, would be required to control material movement from each channel into the intersection. Similarly, in a system having a simple "T" intersection where three channel segments communicate at the intersection, control of material transport at the intersection would require at least three separate electrical control nodes, typically disposed at the unintersected termini of the channel segments. Furthermore additional added intersections typically require the addition of at least one new electrode to control material transport at the new intersection. Specifically, a channel network made up of a main channel intersected at two different points by two separate channels, e.g., two "T" intersections, requires four separate electrodes disposed at the unintersected termini of the channel segments.

Based upon the foregoing, it can be seen that microfluidic systems having multiple intersections typically required a large number of electrodes to control material transport at those intersections. Specifically, a system having n intersections would typically require at least (n+2) electrodes, to control material transport at those intersections (assuming the simplest geometry of a main channel intersected by multiple other channels at multiple "T" intersections). For more complex systems, e.g., parallel channels disposed between two common, transverse channels, even more electrodes are required, e.g., n+4 electrodes. Rephrased, in typically described microfluidic systems, the number of intersections is always less than, and often, far less than the number of electrodes used to control material transport at those intersections.

The microfluidic devices and systems of the present invention, on the other hand, include a plurality of intersecting microscale channels that include at least n channel intersections, and x electrical control nodes at the unintersected channel termini, as described above. In these devices, however, the number of channel intersections (n) is always greater than or equal to the number of electrical control nodes disposed at unintersected channel termini (x), provided that there are at least 2 channel intersections, preferably, at least 3 channel intersections, and at least 2 electrical control nodes. The devices of the present invention optionally include at least 4, 5, 10 or even 20 or more channel intersections. Accordingly, the devices of the present invention optionally include at least 3, 4, 5, 10 or even 20 different electrical control nodes.

By way of example, a microfluidic device that incorporates 10 parallel channels connecting two transverse channels includes 20 intersections, 1 intersection where each parallel channel (10) intersects each transverse channel (2). Material transport at these 20 intersections can be controlled according to the present invention, by simply controlling the potentials applied at the termini of the transverse channels, of which there are 4. This compares favorably to the use of electrodes at the termini of each parallel channel to control material transport at the intersection of these channels with the transverse channels. In particular, such a system in the example provided, would require the four electrodes described above, as well as an additional 20 electrodes at each parallel channel terminus, for a total of 24 or (n+4) electrodes.

For purposes of clarification, as used herein, the term "intersection" refers to a point in a microfluidic channel system or network at which three or more channels or channel segments are in fluid communication. Thus, as alluded to above, an intersection includes a simple "T" intersection, at which three channel segments communicate, as well as a simple cross or four-way intersection. Other types of intersections are also included within this definition, including, e.g., radial intersections, also termed "wagon wheel" intersections, at which larger numbers of channel segments, e.g., five or more, are in fluid communication.

A number of different channel geometries and layouts can be utilized to provide substantially equal currents in interconnected parallel channels, while requiring a minimum number of electrical control nodes. Several of these geometries are illustrated in FIGS. 3–5 and FIG. 8.

Figure 3:
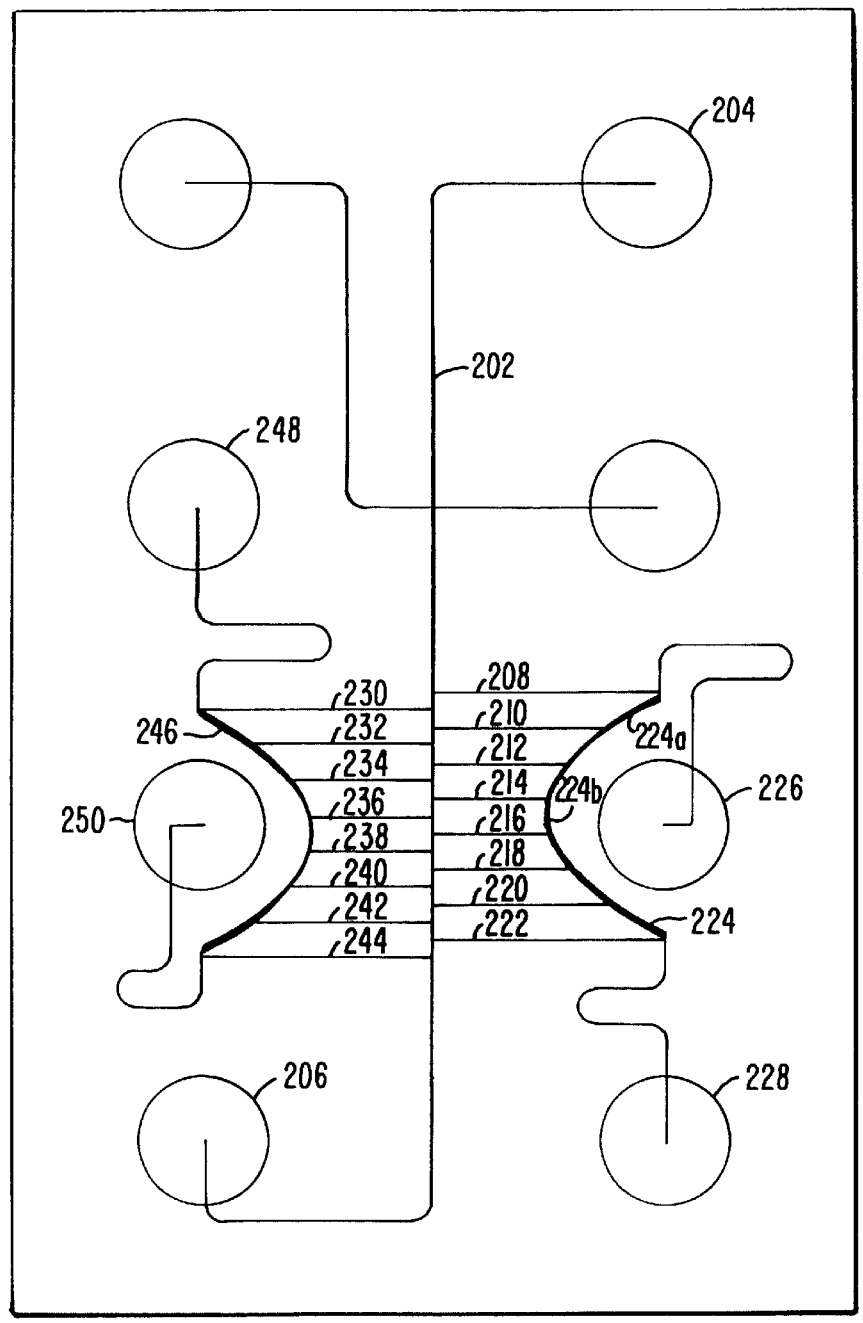
FIG. 3 illustrates an embodiment of a channel layout in a microfluidic device for directing fluids or samples serially introduced into the device into a number of parallel channels.

For example, in one embodiment, FIG. 3 illustrates a microfluidic device fabricated from a planar substrate 200. The device employs a channel orientation that may be used to accomplish serial to parallel conversion or equal fluid flow in parallel channels. The substrate 200 includes main channel 202, which includes electrodes disposed in each of ports 204 and 206, at the termini of channel 202. A series of parallel channels 208–222 and 230–244 terminate in main channel 202. The opposite termini of these parallel channels are connected to parabolic channels 224 and 246, respectively. Electrodes are disposed in ports 226, 228, 248 and 250, which are included at the termini of these parabolic channels, respectively. Thus, in the device shown, material transport at the intersections of channels 208–222 and 230–244 with parabolic channels 246 and 224, respectively, as well as transverse channel 202, is controlled by application of appropriate voltages at reservoirs 204, 206, 226, 228, 248 and 250. Thus, application of voltages at 6 reservoirs controls material transport and direction at 32 different channel intersections. The overall device shown includes 33 channel intersections and only 8 reservoirs at which voltages are applied, also termed electrical control nodes.

In operation, a fluid or sample plug is pumped along main channel 202 by applying a voltage gradient between electrodes 204 and 206. An equal voltage gradient is applied between electrodes 226 and 228, and 248 and 250, resulting in a net zero flow through the parallel channels. Specifically, no voltage gradient exists along the length of these parallel channels.

The sample may be present within main channel 202 as a long slug of a single sample, or multiple slugs of a single or multiple samples. Once the sample material or materials reach the intersection of the main channel with the parallel channels, e.g., 230–244, it is then directed into and through the parallel channels by applying a potential gradient between electrodes 226:246, and 228:248, which results in a material transport from parallel channels 208–222, to force the samples into parallel channels 230–244. The resistance, and thus the current flow, in each of the parallel channels 208–222 and 230–244 is maintained constant by adjusting the length of the parallel channels, resulting in a parabolic channel structure connecting each of the parallel channels to its respective electrodes. The resistance within the parabolic channel between parallel channels is maintained constant by adjusting the channel width to accommodate variations in channel length resulting from the parabolic shape of the overall channel. For example, channel segment 224a, while longer than channel segment 224b, will have the same resistance, because segment 224a is appropriately wider. Thus, the parabolic design of channels 224 and 246, in combination with their tapering structures, results in the resistance along all of the parallel channels being equal, resulting in an equal fluid flow, regardless of the path chosen. Generally, determining the dimensions of channels to ensure that the resistances are equal among the channels, may be carried out by well known methods, and generally depends upon factors such as the make-up of the fluids being moved through the substrates.

Figure 4:
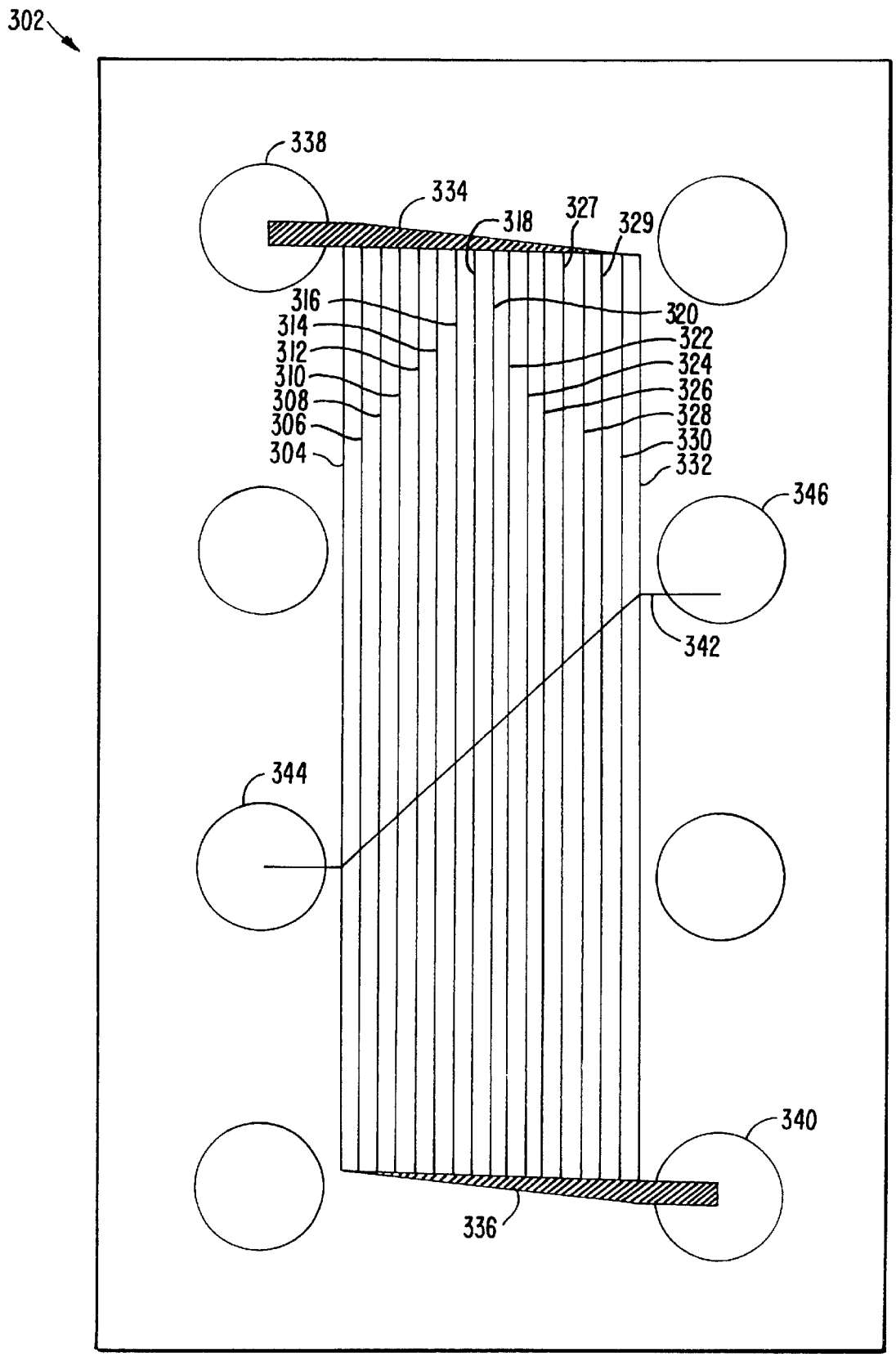
FIG. 4 illustrates a microfluidic device incorporating an alternate channel layout for directing materials, fluids or samples serially introduced into the microfluidic device into a plurality of parallel channels.

In another example, FIG. 4 illustrates how the principles of the present invention can be used in a substrate design that employs fewer electrodes to affect parallel fluid flow. In particular, fluid flow within an array of parallel channels is controlled by a single pair of electrodes. As shown, substrate 302 includes a plurality of parallel channels 304–332. These parallel channels each terminate in transverse channels 334 and 336. Transverse channel 334 has a tapered width, going from its widest at the point where it intersects the nearest parallel channel 304 to the narrowest at the point it intersects the most distant parallel channel 332. Transverse channel 336, on the other hand, goes from its widest at the point it intersects parallel channel 332, to the narrowest where it intersects parallel channel 302. Electrodes are included in the ports 338 and 340 at the wider termini of transverse channels 334 and 336, respectively. The dimensions of these tapered channels are such that the current flow delivered through each of the parallel channels, via the tapered channels, is substantially equal, thereby permitting equal flow rates in each of the parallel channels. As shown, transverse or sample introduction channel 342 is oriented so that it crosses each parallel channel at the same point relative to one or the other electrode, to ensure that the potential at the intersection of transverse channel 342 is the same in each of the parallel channels, again, to prevent the formation of transverse electrical fields, or "shorting out" the array of channels. This results in the sample introduction channel 342 being disposed across the parallel channels at a nonperpendicular angle, as shown.

In operation, a sample fluid, e.g., disposed in port 344, is flowed through transverse channel 342, and across the intersection of the parallel channels 304–332 by applying a potential across ports 344 and 346. Once the sample is disposed across the one or more desired parallel channels, e.g., as dictated by the serial to parallel conversion desired (see FIGS. 2A–2D), a potential is then applied across ports 338 and 340, resulting in an equal fluid flow through each of the parallel channels and injection of the sample fluid into each of the desired parallel channels.

Figure 5:
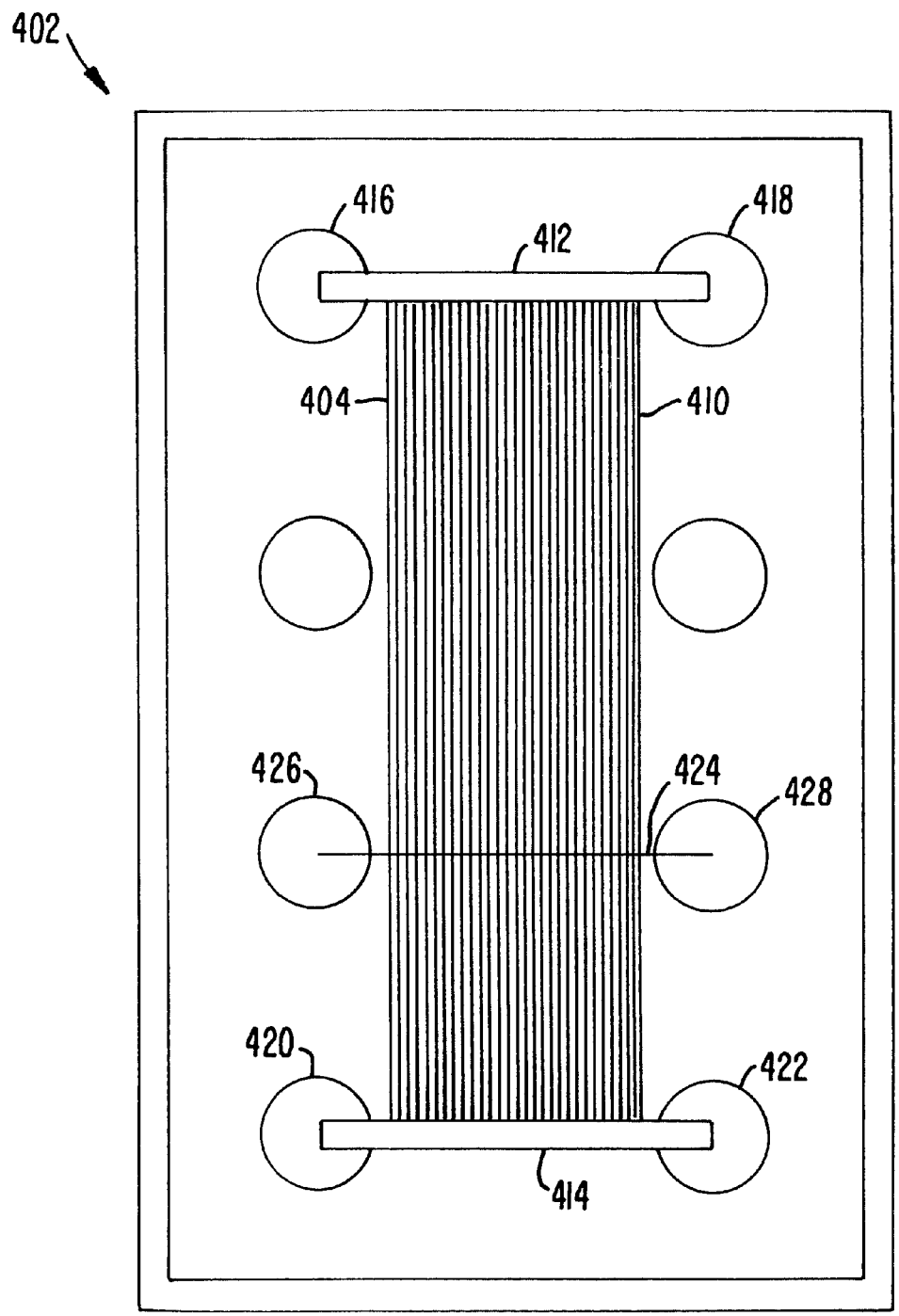
FIG. 5 illustrates a microfluidic device incorporating another alternate channel layout for directing materials, fluids or samples serially introduced into the microfluidic device into a large number of parallel channels.

FIG. 5 illustrates still another embodiment for practicing the principles set forth herein. In this embodiment, a substrate includes a large number of parallel channels. For ease of discussion, these channels are referred to herein as parallel channels 404–410, although it should be understood that preferred aspects will include upwards of 50, 100, 500 or more separate parallel channels. The parallel channels 404–410 terminate at one end in transverse channel 412 and at the other end in transverse channel 414. Electrodes are provided within ports 416 and 418, and 420 and 422 at the termini of these transverse channels. In this embodiment, the problems of varying current within the different parallel channels are addressed by providing transverse channels 412 and 414 with sufficient width that current variation across the length of these transverse channels, and thus, as applied to each parallel channel, is negligible, or nonexistent. Alternatively, or additionally, a single electrode may be disposed along the length of each of these transverse channels to ensure equal current flow at the transverse channel's intersection with each parallel channel.

As shown, however, transverse or sample introduction channel 424 intersects each of the parallel channels, and is controlled by electrodes disposed within ports 426 and 428 at the termini of channel 424. As described for FIG. 4, above, the sample introduction channel intersects each parallel channel at a point where the potential applied to each channel will be equal. In this aspect, however, the channel is arranged substantially parallel to transverse channels 412 and 414, as each parallel channel is subjected to the same current.

In operation, a sample, e.g., disposed in port 426, is flowed through sample channel 424, across the intersection of the various parallel channels 404–410, by applying a potential across ports 426 and 428. Once the sample fluid is in its appropriate location, i.e., across all or a select number of parallel channels, a potential is applied across ports 416:420 and 418:422, injecting a plug of sample into the parallel channels.

Figure 8:
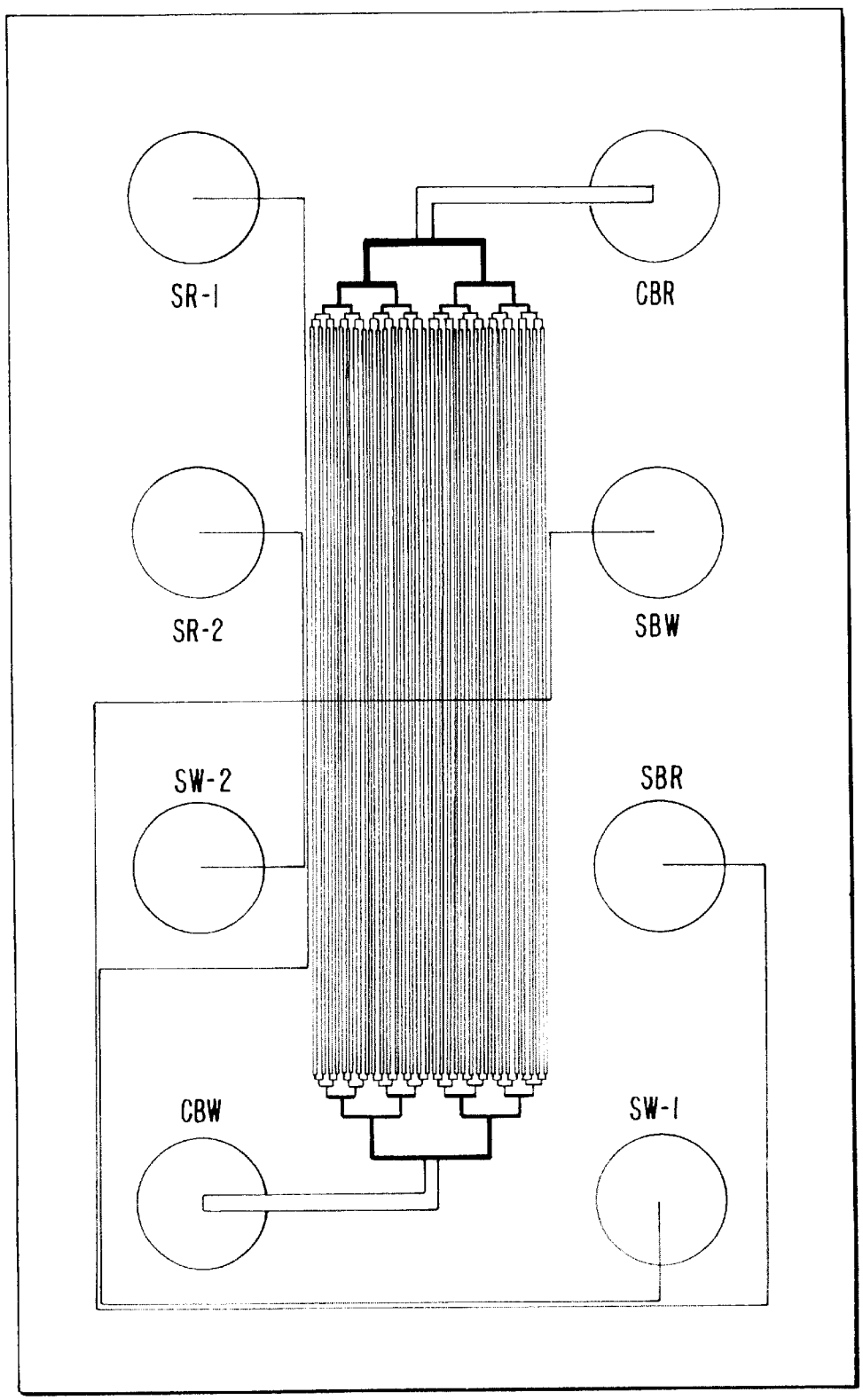
FIG. 8 is a schematic illustration of a device for use in performing multiple electrophoretic separations, in parallel, of a sample or samples introduced into the device, serially.

An alternate, although similar channel geometry for a serial to parallel conversion device is shown in FIG. 8. As shown the device includes an array of parallel channels where each channel is coupled between two reservoirs/electrical nodes (CBR and CBW). Equal currents are applied to the parallel channels via fractal channel networks at each end of the parallel channel array. Sample is introduced via a central channel introduction channel (disposed between and coupled to reservoirs SBW and SBR). Additional channels are provided to introduce additional elements to the sample material, or additional samples, prior to introduction into the parallel array (channels disposed between and coupled to reservoirs SR-1 and SW-1 or SR-2 and SW-2). The fractal channel networks have wider cross-sections in order to ensure optimal current is delivered to the parallel channel array, e.g., minimize resistance.

Although the present invention is exemplified in terms of utilizing either a parabolic channel geometry or a wide channel geometry to ensure equal resistances in parallel channels, it will be readily appreciated that both accomplish substantially the same goals, and further that a combination of wider channel geometries and parabolic channel geometries in those channels connecting the termini of the parallel channels, is often used to optimize for maintaining applied currents in an acceptable range (wider channels require greater applied currents) and minimizing the use of substrate area (parabolic channel geometries typically utilize greater substrate areas than straighter channels). Thus, in preferred aspects,

EXAMPLES

1. Parallel Transport of Fluorescent Material in Interconnected Parallel Channels A microfluidic device was fabricated from a glass base substrate having another glass substrate overlaying the first. The device included a channel layout as shown in FIG. 4. The device was filled by capillary action using a sodium tetraborate buffer placed into one of the reservoirs. Fluorescein mixed with the running buffer, was placed into reservoir 344 and drawn across the intersections with the parallel channels by applying a voltage gradient between reservoirs 344 and 346.

Once the fluorescein filled the entire transverse channel 342, the voltage gradient was changed from between reservoirs 344 to 346, to between reservoirs 338 and 340. Because of the geometry of the transverse channels 334 and 336, as well as the angled geometry of transverse channel 342, the amount of current passing through each of parallel channels 304–332 was maintained substantially equal, and the fluorescein plugs were transported down their respective channels at substantially the same rate.

Figure 6:
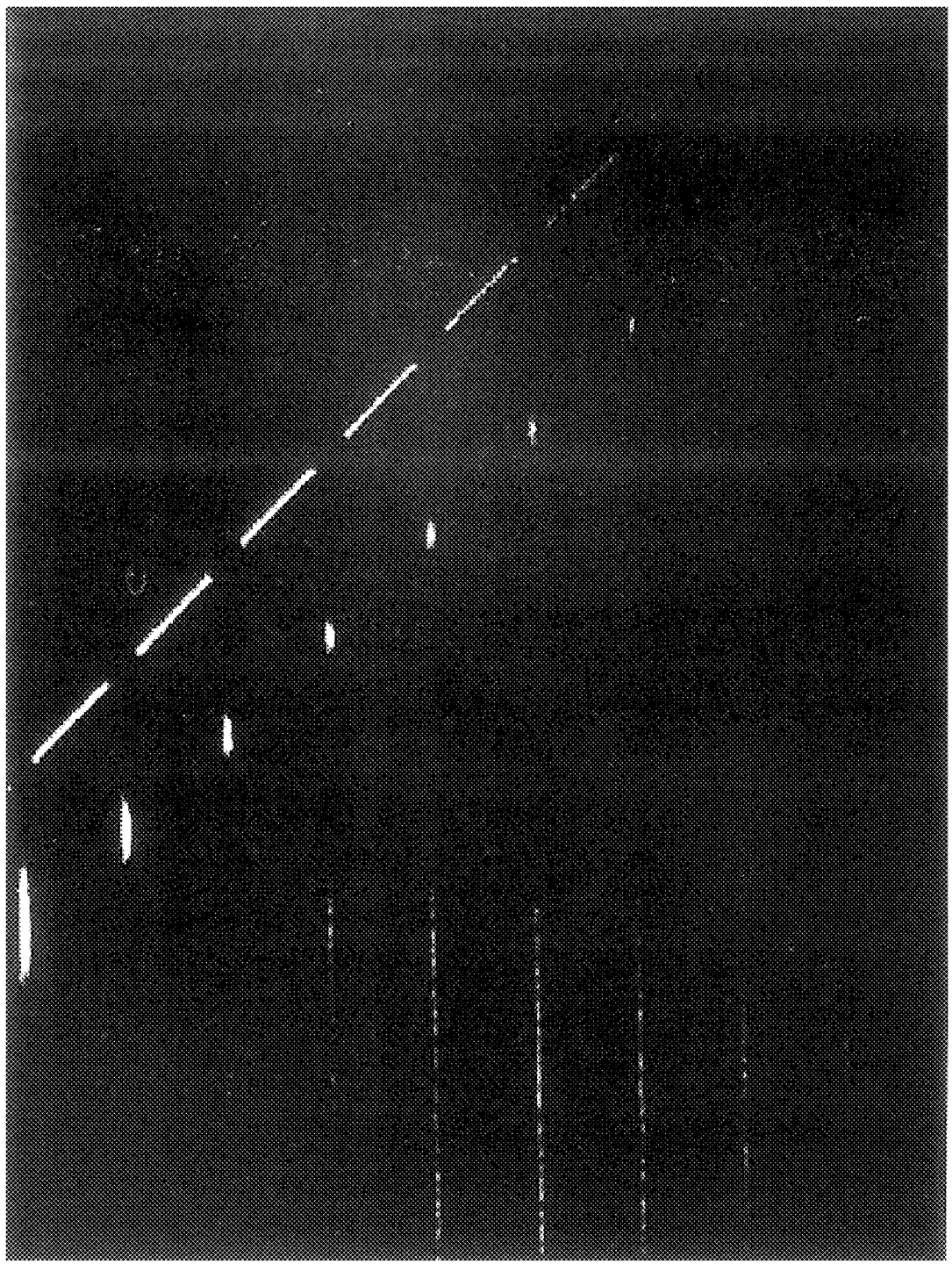
FIG. 6 is a photograph showing the injection of separate fluorescent material plugs (light area) into multiple parallel channels, as schematically illustrated in FIG. 2A, in a microfluidic device employing the geometry shown in FIG. 3.
Figure 7A:
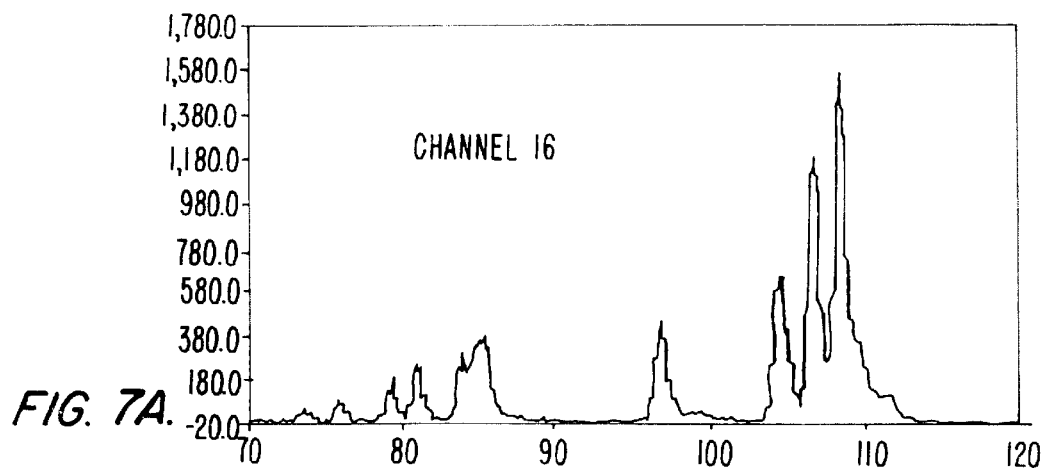
FIGS. 7A–E show size based separation of nucleic acid fragments in five parallel, interconnected channels within a single microfluidic device.
Figure 7B:
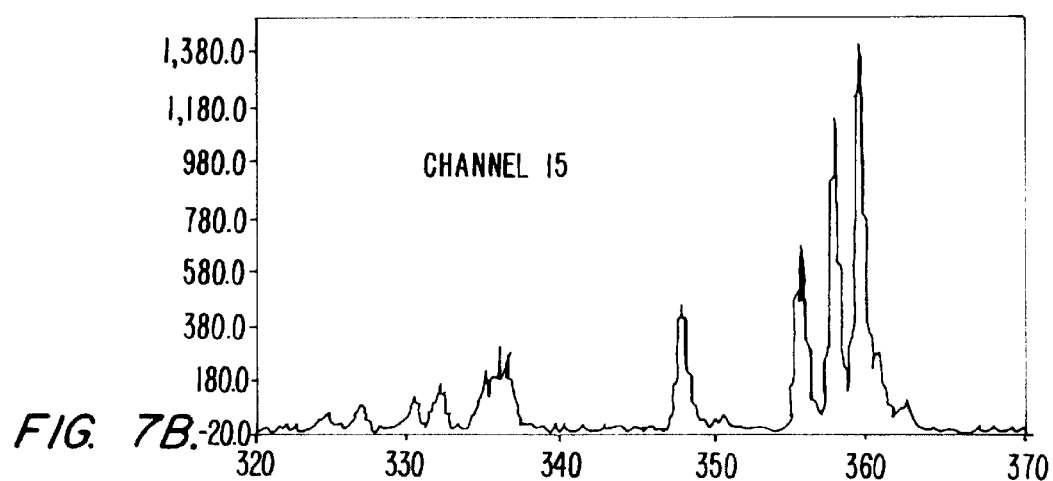
Figure 7C:
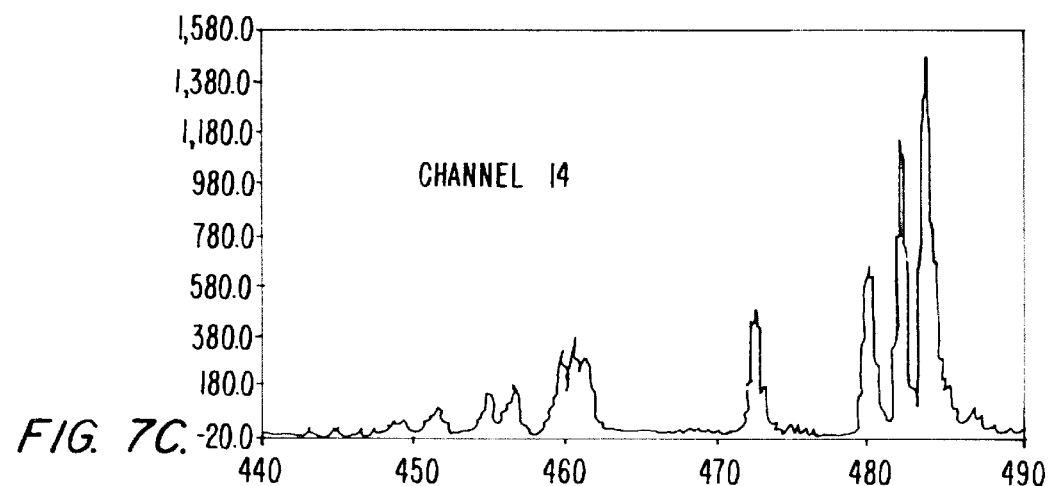
Figure 7D:
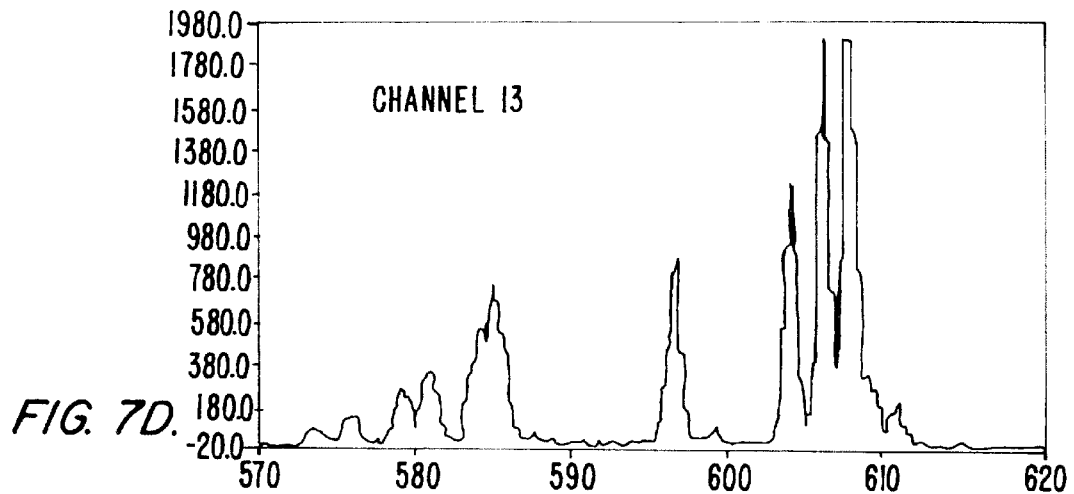
Figure 7E:
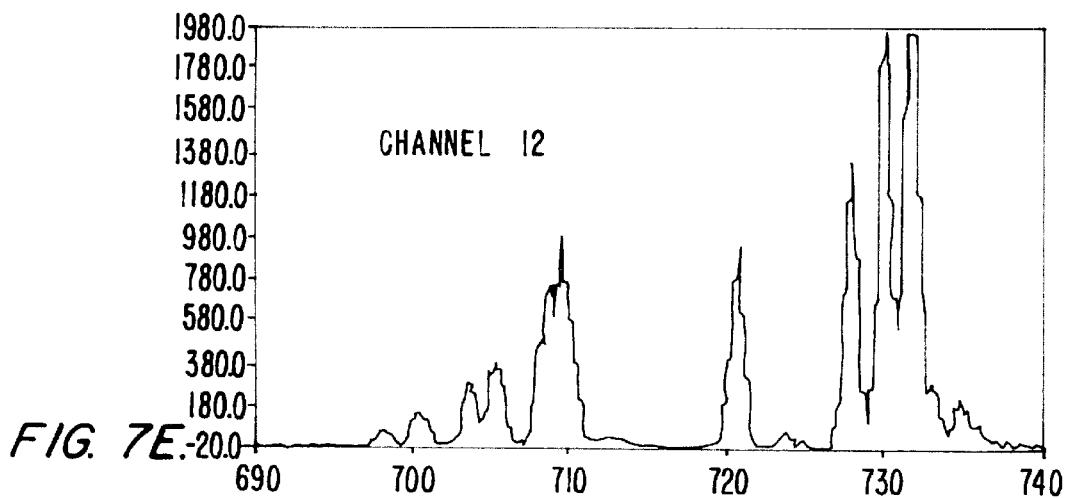

FIG. 6 is a photograph illustrating the introduction of fluorescein into the array of parallel channels. As can be seen from this photograph, the fluorescent plugs in each channel are moving at substantially the same rate.

2. Parallel Analysis of Nucleic Acid Fragments in a Microfluidic System

A microfluidic device fabricated from two bonded glass layers, and having the channel geometry shown in FIG. 8, was used to analyze the same mixture of nucleic acid fragments in 32 parallel channels, where the samples were serially introduced into the device via the central sample channel. Currents were maintained substantially constant from one parallel channel to the next, by using only two reservoir/electrodes to control material movement in those parallel channels. The two reservoir/electrodes (labeled CBR ad CBW) were connected to the parallel channels via corresponding fractal channel networks. The sample to be tested was placed in the sample well (SR-2) and transported across the parallel channel array by transporting the sample to the sample waste well (SBW).

The sample solution was a combination of 3.5% Genescan polymer sieving matrix in the Genescan buffer, a 500:1 dilution of the SYBR Green intercalating dye, and 5:1 dilution of a 1 $\mu g/\mu L$ solution of double-stranded DNA size standard, $\Phi$X174 cleaved with HaeIII (Promega Corp.). The microfluidic device was first filled with a 3.5% solution of the GeneScan™ polymer in the Genescan buffer, including a 500:1 dilution of the SYBR Green intercalating dye. This solution was placed in all wells, except well SR-2, which was filled with the DNA sample solution.

The experiment consisted of first filling the loading channel with DNA solution by applying a potential between wells SR-2 and SBW. A small amount of sample was then injected in the parallel separation channels by briefly applying a potential between wells CBW and CBR. The loading channel was then cleared out by applying a potential between wells SW-2 and SBW. This clearing out ensured that only a limited amount of DNA was injected into each separation channel. Finally, the separation was done in each channel simultaneously, by again applying an electric potential between wells CBW and CBR. The separation was observed at a location at the bottom of the separation channels, near well CBW.

Detection of separated species was carried out using a single detector utilizing a Nikon inverted Microscope Diaphot 200, with a PTI Model 814 PMT detection system, for epifluorescent detection. An Opti-Quip 1200–1500 50W tungsten/halogen lamp coupled through a 40X microscope objective provided the light source. Excitation and emission wavelengths were selected with a FITC filter cube (Chroma, Brattleboro Vt.) fitted with appropriate filters/dichroic mirrors. Five separate runs were performed where sample was loaded through the main channel and simultaneously injected into each of the 32 parallel separation channels. In each separate run, detection was carried out at a different one of the 32 channels.

The separation of the different fragments in each of five different parallel channels is shown in FIG. 7, as retention time vs. fluorescent intensity. The retention time is shown as the time from the first injection. The specific channel is indicated for each separation. Since only a single detector was used, each plot is a different sample of one of the 32 separations that were in fact done simultaneously each time a sample was injected. The similarity of each scan indicates that similar amounts of material were injected into each channel, and further, that relative retention times, e.g., electrophoretic mobilities, in each channel were maintained substantially constant.

While the foregoing invention has been described in some detail for purposes of clarity and understanding, it will be clear to one skilled in the art from a reading of this disclosure that various changes in form and detail can be made without departing from the true scope of the invention. All publications and patent documents cited in this application are incorporated by reference in their entirety for all purposes to the same extent as if each individual publication or patent document were so individually denoted.

What is claimed is:

1. A microfluidic device, comprising:
    a body structure;
    a plurality of integrated channels disposed in the body structure, the plurality of integrated channels comprising:

at least a first transverse channel;

at least first and second side channels disposed on a first side of the transverse channel, each of the first and second side channels having first and second ends, the first ends of the first and second side channels intersecting the transverse channel, and the second ends of the first and second side channels being in fluid communication with at least a first source of first material;

at least third and fourth side channels disposed on a second side of the transverse channel, each of the third and fourth channels having first and second ends, the first ends of the third and fourth channels being in fluid communication with the transverse channel, and the second ends of the third and fourth channels being in fluid communication with a waste reservoir; and a material transport system for transporting a second material into the transverse channel, and for transporting portions of the second material into the third and fourth channels by directing a flow of first material from the first source, through the first and second channels into the transverse channel, the material transport system comprising one or more electrode disposed in electrical contact with the waste reservoir, or the first or second ends of the first, second, third or fourth microchannels, or the first source, wherein an electrical current path between the one or more electrode and an additional electrode through the first side channel provides substantially equal resistance to a resistance between the one or more electrode and the additional electrode through the second side channel.

2. The microfluidic device of claim 1, comprising one or more electrode disposed within the waste reservoir, or proximal to the first or second ends of the first, second, third or fourth microchannels, or disposed within the first source.

3. A method of directing one or more sample materials serially introduced into a microscale channel, into a plurality of parallel channels fluidly connected to the microscale channel, the method comprising:

providing a microfluidic device having at least a first microscale transverse channel, at least first and second microscale side channels intersecting a first side of the transverse channel, and at least third and fourth microscale side channels intersecting a second side of the transverse channel;

introducing the one or more sample materials serially into the first transverse channel; and directing at least a portion of the one or more sample materials into the at least third and fourth channels by directing material into the transverse channel from the first and second channels by applying an electrical current between a first voltage source in electrical communication with an end of the first and second side channels and a second voltage source in electrical communication with an end of the third side channel, wherein an electrical current path between the first voltage source and the second voltage source via the third channel has substantially the same electrical resistance via the first side channel as via the second side channel.

4. The method of claim 3, further comprising applying a current between a first voltage source and a second voltage source to electrokinetically transport at least a portion of the at least one material into each of the first and second side channels.

5. The method of claim 4, wherein the introducing step includes applying a separate current from each of the first and second voltage sources to the first transverse channel to provide a pinching flow of current from each of the first, second and third side channels, into the first transverse channel.

6. The method of claim 3, wherein the channel network includes a plurality of intersecting microscale channels, the plurality of microscale channels comprising n channels and x unintersected channel termini, wherein x is less than or equal to n, and provided that x is at least 2 and n is at least 3.

7. The method of claim 6, comprising applying a separate selected electrical potential to at least three of the x reservoirs simultaneously, whereby material is controllably moved at the n intersections.

* * * * *